United States Patent
Weber et al.

(10) Patent No.: US 8,357,504 B2
(45) Date of Patent: Jan. 22, 2013

(54) METHOD AND KIT FOR THE MICROBIOLOGICAL DETERMINATION OF VITAMINS IN SUBSTANCE MIXTURES

(75) Inventors: Wolfgang Weber, Berlin (DE); Franz Paul Armbruster, Bensheim (DE)

(73) Assignee: IFP Privates Institut fur Produktqualitat GmbH, Berlin (DE)

( * ) Notice: Subject to any disclaimer, the term of this patent is extended or adjusted under 35 U.S.C. 154(b) by 579 days.

(21) Appl. No.: 11/658,804

(22) PCT Filed: Aug. 1, 2005

(86) PCT No.: PCT/EP2005/008318
§ 371 (c)(1),
(2), (4) Date: Apr. 2, 2007

(87) PCT Pub. No.: WO2006/013078
PCT Pub. Date: Feb. 9, 2006

(65) Prior Publication Data
US 2008/0044846 A1    Feb. 21, 2008

(30) Foreign Application Priority Data

Jul. 30, 2004  (DE) .......................... 10 2004 037 062
Jan. 25, 2005  (DE) .......................... 10 2005 003 457

(51) Int. Cl.
*C12Q 1/02* (2006.01)
(52) U.S. Cl. .............................. 435/29; 435/4; 435/6.15
(58) Field of Classification Search .................. None
See application file for complete search history.

(56) References Cited

U.S. PATENT DOCUMENTS 4,879,239 A * 11/1989 Daggett et al. ............. 435/252.1

OTHER PUBLICATIONS

The term "Conserve"—definition by Merriam Webster's online dictionary, at the web at http://www.merriam-webster.com, pp. 1-2; accessed on line on Sep. 12, 2009.*
Soelve M. et al. Automated microbiological assay for quantitation of niacin performed in culture microplates read by digital image processing, Food Chemistry (1994), vol. 49, No. 4, pp. 419-26, entire document.*
Zayed et al., Influence of Trehalose and Moisture Content on Survival of *Lactobacillus salivarius* Subjected to Freeze-Drying and Storage, 39 *Process Biochemistry* 1081-1086 (2004).
Kelleher et al., "Cryo-preservation of *Lactobacillus leichmannii* for Vitamin $B_{12}$ Microbiological Assay," 47 *Medical Laboratory Sciences* 90-96 (1990).
Stapert et al., "The Effect of Freezing and Thawing on Cellular Function in *Lactobacillus leichmannii*," 4 *Cryobiology* 174-76 (1968).
de Valdez et al., "Protective Effect of Adonitol on Lactic Acid Bacteria Subjected to Freeze-Drying," 45 *Applied and Environmental Microbiology* 302-304 (1983).
"Microbiological Ultramicro-analysis," Patent Abstracts of Japan No. 081 (C-014) (Jun. 11, 1980).
"Microbial Determination of Water-Soluble Vitamins," Patent Abstracts of Japan No. 575 (C-1011)(Dec. 15, 1992).

* cited by examiner

*Primary Examiner* — Jon P Weber
*Assistant Examiner* — Satyendra Singh
(74) *Attorney, Agent, or Firm* — James C. Lydon

(57) ABSTRACT

Method for the quantitative determination of vitamins, amino acids, or other substances necessary for life, in a substance mixture, whereby in the culture container, the cavities of a microtitration plate, in each case a predetermined number of vital cells of a suitable microorganism are prepared in a permanent manner. For this purpose, the cells are shock frozen at −80° C. and then freeze dried in a freezing solution containing 200 to 500 mM trehalose/sucrose. The freezing solution is preferably the test medium. The culture containers are preferably the wells of a microtitration plate.

9 Claims, 4 Drawing Sheets

Fig. 1

Niacin Calibration

Fig. 2

Folic Acid Standard Curve

Fig. 3

Vitamin B12 Calibration

Fig. 4

Biotin Calibration

Fig. 5

Vitamin B6 Calibration

Fig. 6

Calibration Ca Pantothenate

Fig. 7

METHOD AND KIT FOR THE MICROBIOLOGICAL DETERMINATION OF VITAMINS IN SUBSTANCE MIXTURES

FIELD OF THE INVENTION

The invention relates to a method and a kit for the quantitative determination of substances important for life in substance mixtures in general and in particular in foodstuffs, feedstuffs, cosmetics, medicaments, pharmaceutical products, body fluids, medical and other analytical samples.

BACKGROUND OF THE INVENTION

By vitamins one understands substances necessary for life, that the organism must take up from foods. With a balanced diet, the human daily requirement for vitamins is fully satisfied. In the case of an inadequate or faulty diet, or a resorption disruption, a vitamin deficiency can arise and lead to diseases such as scurvy, beri beri, night blindness and even death. Dietary supplement products such as soya milk for infants are therefore supplemented with vitamins. Foodstuffs are also otherwise supplemented with vitamins. The biological activity of vitamins is structure dependent; it is indicated in weight units or international units (IE or EU). The vitamin content of a sample is, however, difficult and time consuming to determine. This applies in particular for the water soluble vitamins and the trace vitamins $B_{12}$, folic acid and biotin.

One can determine the vitamin content in a substance mixture (i) by means of chemical-physical methods, e.g., by means of high pressure liquid chromatography (HPLC). These are too insensitive for trace vitamins such as vitamin $B_{12}$, folic acid and biotin. (ii) With immunology methods. They are not precise enough for many determinations, because of matrix effects, and must be adapted to each sample matrix. Thereby there readily arise interferences with other matrix components, in particular in the case of foodstuffs for infants, feedstuff for cats, serum and blood. (iii) Further, one can determine the vitamin content in animal testing, which is not relevant in practice, and (iv) by means of microbiological methods. Here, there is grown a microorganism, for which the vitamin to be determined is essential, in a specifically deficient nutrient solution, supplemented with a sample or vitamin standard, and the growth thereof or its metabolism are measured at intervals, for example by titration, gravimetrically, by turbidity or nephelometrically. In relation to the background of microbiological determination the following further publications are to be mentioned: GORIN, G. et al. Appl. Microbiol., 1970, 20, 641-642; KELLEHER, B P et al., J. Clin. Pathol., 1991, 44(7), 592-595; BUI, M. H., J. Vitam. Nutr. Res., 1999, 69(5), 362-366; MOLOY, A. M. et al., Methods Enzymol., 1997, 281, 43-53. In microbiological determination one must apply a plurality of dilution series so that at end of the incubation time a growth or metabolic value lies in the measurement range of the parallel standard concentration series. For each testing, a standard curve valid only for this attempt has to be prepared. Further, for reasons of safety and precision, each concentration stage of the standard series and the sample series is to be applied at least three times. The vitamin content of the sample is then determined by means of comparison with the known vitamin content of the parallel standard series. Generally valid precision indications are not possible; the coefficient of variation should, however, lay at around 10 percent or below. The microorganism suspension for the inoculation of the standard and sample series cannot be stored and must be newly grown for each growth testing. There is thus always the uncertainty as to whether the inoculation suspension has been correctly grown or the microorganism has the desired sensitivity and specificity. The microbiological determination of vitamins is very labor and time demanding, and it requires considerable laboratory organization. Only very few laboratories in the field of foodstuffs have specialized in this kind of analysis. Laboratory doctors have ceased to use this method in human diagnosis because of the great outlay, although until today no equally good method for the determination of the biologically active vitamin content is available. Microbiological determination is, however, as before the reference method for all other methods.

SUMMARY OF THE INVENTION

It is the object of the invention to make available an improved method and a kit for the microbiological determination of vitamins, amino acids, in particular lysine, methionine or cystine, and other substances important for life such as choline or inositol, which does not have the disadvantages of the state of the art and is fundamentally capable of being automated.

This object is achieved by means of a method for the quantitative microbiological determination of individual vitamins, amino acids, or other substances necessary for life, in a substance mixture, with which in the culture container for the microbiological determination of growth and metabolism a predetermined number of vital cells of a suitable microorganism, after the addition of conserving sugars, shock freezing and freeze drying, are stored dry. For this purpose the cells are shock frozen and freeze dried in a freezing solution containing additionally 200 to 500 mM trehalose/sucrose, preferably 200 to 250 mM trehalose. The freezing solution is preferably the test medium for the biological determination. In the method, by the cells are shock frozen at a temperature between −10 and −100° C., preferably between −18 and −80° C. The test equipment or kit in accordance with invention includes microorganisms preserved in this way in predetermined number in one or more culture containers for the growth testing in microbiological determination. The culture containers are preferably wells of a microtitration plate.

The method in accordance with the invention distinguishes itself in that an exact number of cells of a suitable microorganism are so conserved in a testing container in the presence of a non-reducing, conserving sugar and an assay specific nutrient medium that the cells can be stored at room temperature for longer periods of time and that after addition of liquid all cells homogeneously grow further. The drying and preserving is effected with slight modification, depending on the organism, through freeze drying, wherein the microorganisms are shock frozen at −80° C. and then freeze dried in a small volume, preferably 0.5 to 100 microliter, particularly preferably 1 to 10 microliter. The non-reducing, conserving sugar is preferably trehalose. There could also be added saccharose (sucrose) and simple sugar such as dextrose, in order to counter drying damage to the microorganism. The concentrations preferably used are 200 to 500 mM trehalose (with or without sucrose), preferably 200 to 350 mM trehalose/sucrose, particularly preferably 200 to 250 mM trehalose/sucrose. The trehalose concentration should be at least amount 200 mM. The addition of divalent ions such as $Ca^{2+}$ upon drying improves the growth start. In order to avoid that the microorganisms, upon freeze drying and dry storage, adjust their metabolism to a deficient environment, they are preferably shock frozen and freeze dried in the later assay medium, naturally in the absence of the substance to be determined. Through this it is avoided that during the freeze drying and dry storing microorganisms are generated which could grow without the substance, the vitamin, to be determined. Such microorganisms otherwise form regularly, lead to a high measurement background and in individual cases to false results.

The kit is provided as an intermediate product of the method in accordance with the invention. The testing kit for the microbiological determination of vitamins includes prepared reagents such as calibrated standards and nutrient solutions for the preparation of the growth curves. It is known to the skilled person that the metabolism of microorganisms can be determined by metabolic end products such as ethanol or lactic acid. The test kid then contains reagents for the detection of these metabolic end products, for example by a suitable color reaction. The growth of the bacteria can also be elegantly determined chemoluminimetrically via the ATP content after disassociation of the bacterial wall and through addition of luciferin and luciferase.

The method in accordance with the invention is in principle suitable for the microbiological determination of content of all vitamins, vitamin precursors, vitamin derivatives, amino acids and other substances important for life. In particular it recommends itself for the detection of trace vitamins. As examples there are mentioned:

Microorganism for the Detection

The most important biological vitamin active substances are indicated in each case in brackets.

| | |
|---|---|
| Vitamin $B_{12}$ (cyanocobalamin, hydroxycobalamin) | Lactobacillus delbrueckii subsp. lactis (L. leichmanii) ATCC 7830 |
| Folic acid (Folic acid, pteroylglutamine acid Folic acid conjugate) | Enterococcus hirae ATTC 8043 Lactobacillus rhamnosus ATCC 7469 |
| Biotin | Lactobacillus planatarum ATCC 8014 |
| Pantothenic acid (Pantothenic acid, panthenol) | Lactobacillus planatarum ATTC 8014 |
| Niacin (Nicotinic acid, Nicotinic acid amide) | Lactobacillus planatarum |
| Vitamin $B_1$ (thiamine, thiamine pyrophosphate) | Lactobacillus fermentus ATCC 9338 Weisella (lactobacillus) viridescens ATCC 12706 |
| Vitamin $B_2$ (riboflavin, riboflavin phosphate) | Lactobacillus rhamnosus ATCC 7469 Lactobacillus helveticus |
| Vitamin $B_6$ (pyridoxine, pyridoxal, pyridoxamine, pyridoxal-5'-phosphate) | Saccharomyces cerevisiae ATCC 9080 Saccharomyces faecalis |
| Choline | Neurospora crassa ATCC 9277 |
| Inositol | Saccharomyces cerevisiae ATCC 9080 |
| Lysine, methionine, cystine | Pediococcus acidilactici ATCC 8042 |

A particular advantage of vitamin determination in accordance with the invention is that, alongside the saving of work and time, also all biologically similarly acting compounds are determined. This has for the fields of foodstuffs and human diagnosis many advantages:

Foodstuffs field, with the example of nicotinic acid and nicotinic acid amide. Both forms are similarly vitamin active. As a rule only niacin is declared, even when both forms of the vitamin are present. The microbiological determination detects both compounds.

Human diagnosis: Here also, the microbiological analysis is advantageous. Up to now, serum analyses have been falsely interpreted, since the conventional methods only detect individual forms of a vitamin. The microbiological analysis provides the true biologically active vitamin content.

It is surprising that the method in accordance with the invention provides reproducible growth curves with the standard and the sample. For decades microorganisms have been kept in glycerin and other freezing solutions or in liquid nitrogen. Also lyophilisation and drying of microorganisms and spoors was known. The state of the art further teaches the drying and storing of prokaryotic microorganisms or viruses in the presence of trehalose and divalent cations, e. g. in the wells of a microtitration plate, if a closed cold chain is to be avoided (see U.S. Pat. Nos. 6,610,531; 5,149,653). The goal of these storage methods is, however, the basic viability of the microorganisms and retention of genetic and immunological identity. On the other hand it was also known that after longer storage, for example in a freezing solution, microorganisms need differently long periods of time until metabolism and growth take place. If the microorganisms were, after freezing, transferred to a culture solution, than as a rule the microorganism which most rapidly regenerates and first begins to grow would outgrow all other microorganisms in the solution. With the most rapidly growing microorganism, an organism is preferred which is different from the normally growing organisms. Up to now, further, one assumed that any form of long-term storage would lead to differently long growth delays upon reconstitution. The combination of microbiological vitamin determination and the freeze drying of an exact number of microorganisms in the presence of a conserving sugar such as trehalose in a culture container such as the well of a microtitration plate or an Eppendorf container was not known. It was also not known that after addition of water and nutrient medium these microorganisms in their entirety begin to grow without delay, so that they can be employed for controlled growth tests, such as effected in microbiological vitamin determination.

The advantage of the method in accordance with the invention rests in that the microorganism for the vitamin determination no longer needs to be newly grown, but is present in the wells of a microtitration plate in defined number and constitution. Therewith, for the testing laboratory, all growth and dilution steps are dispensed with. There need only to be to be added to the individual wells of the microtitration plate exact quantities of vitamin deficient nutrient medium and sample, or vitamin standard concentrations. Since the microorganisms in the wells across the microtitration plate are always the same, the measurement range is overall less variable. That means that the microtitration plates can be configured for certain incubation times. Also there is a lesser risk of dilution mistakes, since finally only the sample needs to be diluted in simple steps. Solutions with fixed standard concentrations of the vitamin to be investigated may be included in the kit. With this, the standard curves are more dependable. The danger of contamination is reduced. The growth media are characterized and tested in advance for the microorganism concerned. Thus, the vitamin determination can be immediately begun, since the number of microorganisms, state of growth, genotype of the microorganism and test medium have been checked, and for the microtitration plate, the microorganisms and the test media a storage life of at least 12 months can be guaranteed. The plates and the ingredients need only be stored dried and germ-free at room temperature, ideally at 4° C.

By means the microtitration plate, the determination is further adapted to usual ELISA and RIA methods. The microtitration plate technology permits great numbers of samples, the employment of automatic pipetting devices and an automated readout and determination of microorganism growth and metabolic level.

In accordance with the technique of the method, the microorganism suspension is shock frozen and freeze dried in a specific vitamin-deficient solution in the presence of trehalose and/or sucrose. In nature also microorganisms survive in that they protect themselves from complete drying out with a glass-like sugar layer. This natural survival mechanism is exploited in accordance with the invention.

In contrast to frozen storage, in accordance with the trehalose/sucrose dry storage according to the invention the cells are immediately again active upon the addition of liquid or water. The usual freezing shock to the cells does not arise. The stability of the cells is ensured through the addition of trehalose/sucrose to the freezing and storage medium. The trehalose and the sucrose form with the proteins of the cell hydrogen bond connections so that the cells are preserved for months in the natural dry condition. It is evident to provide these cells with alkali- and earth alkali ions such as magnesium, calcium, potassium, sodium. For each species, the buffer for the dry storage and for reconstitution of the microorganisms is to be optimized. As a rule, up to now, conventional Tris and PBS-solutions having each 10 mM $Mg^{2+}$, $Ca^{2+}$, $Zn^{2+}$ have been employed as storage buffers. Although they could be employed, they have the disadvantage that, promoted by the stress of the freeze drying and dry storage, some microorganisms adapt to a deficient environment, mutate or otherwise realign, so that upon the addition of water or sample there are present microorganisms which can grow without vitamin. It is thus advantageous to shock freeze and freeze dry the microorganism in assay medium (without the substance to be determined) in the presence of conserving trehalose/sucrose at −80° C. Determination microorganisms so conserved are stable over periods of months at room temperature, do not change and after the addition of assay medium with and without sample there grow only those microorganisms which need the substance to be determined. Since through this manner of proceeding in fact no microorganisms are present which could grow without the vitamin or the substance to be determined, the growth can be determined in a run-off method. In other words: 48 hours after addition of water and vitamin-containing sample, the microorganisms have then for example multiplied exactly so far that all substance to be determined is consumed. All other substances necessary for growth are present in excess. If the substance to be determined is consumed, the microorganism ceases to grow. Since the determination of end points is very much less prone to error and more convenient than the determination of relative growth speeds, through this the determination is made overall more precise and more reproducible.

The advantage of the dry microorganism microtitration plate in accordance with the invention rests (i) in that with mass production a detailed calibration of the number of cells per well can be effected; (ii) the pre-prepared dry microorganism microtitration plates can be tested in advance for functionality and optimum or minimum incubation times—these values are available to the user as characteristic data of the dried microorganism microtitration plate—and (iii) that a standard microtitration plate having 96 wells permits at the same time a plurality of measurement and comparison series with samples and comparison standards. For the laboratory, there can thus be dispensed with not only the preparation steps (validation studies, testing of the precision of the analyses, characterization of standard and test medium) but all steps can also be effected in an automatic process or by means of automatic analysis devices.

Through the additional water or nutrient medium, the inoculate microorganisms in the wells of the microtitration plate can be homogeneously revitalized for immediate growth tests. Therewith, all reagents for a microbiological vitamin determination can be placed on the market in a ready-to-use kit. Not only that the growth testing can be begun immediately, but in the case of manual analysis this represents generally a substantial facilitation of the work to be carried out, with an increase of quality and precision. The microtitration plate technique further permits an adaptation to full and semi-automatic analysis devices. Further advantages, goals and embodiments of the invention can be understood from the following examples and the drawings.

BRIEF DESCRIPTION OF THE DRAWINGS

There is shown.

DETAILED DESCRIPTION OF PREFERRED EMBODIMENTS

Examples

Example 1

Niacin Determination (Vitamin B3)

1. Preparation of the Microtitration Plate

A culture of *Lactobacillus plantarum* (ATCC 8014) from a glycerol stock was over-inoculated into 10 ml *Lactobacillus* medium and cultivated for 36 hours. The culture was stopped in the logarithmic phase by centrifuging (2500 G×5 minutes), the resulting cell pellet was washed 3× in 0.85% NaCl-solution, suspended in 10 ml 200 mM trehalose, 10 mM $CaCl_2$, and then diluted by about 1 to 10 with Difco™ niacin assay medium, containing casamino acids 12.0 g/L, dextrose 40.0 g/L, sodium acetate 20.0 g/L, L-cystine 0.4 g/L, DL-tryptophane 0.2 g/L, adenine sulfate 20.0 mg/L, guanine hydrochloride 20.0 g/L, uracil 20.0 mg/L, thiamine hydrochloride 200.0 µg/L, calcium pantothenate 200.0 µg/L, pyridoxine hydrochloride 400.0 µg/L, riboflavin 400.0 µg/L, p-aminobenzoic acid 200.0 µg/L, biotin 0.8 µg/L, dipotassium hydrogen phosphate 1.0 g/L, sodium dihydrogen phosphate 1.0 g/L, magnesium sulfate 0.4 g/L, sodium chloride 20.0 mg/L, iron sulfate 20.0 mg/L, manganese sulfate 20.0 mg/L and 200 mM trehalose, 10 mM $CaCl_2$. The dilution was so set that 1 ml of microorganism suspension contained $10^7$ vital microorganisms. 3 µl microorganism suspension was introduced to each well of the microtitration plate, the microorganism suspension in the well was shock frozen in the freezer at −80° C. and the microorganism pellet on the base of the well freeze dried by the application of a vacuum. Each well of the microtitration plate thus contained exactly $3×10^4$ vital microorganisms *Lactobacillus plantarum* in the same stage of growth and this packed into a minute trehalose/sugar/salt pellet. Attention is to be paid that a sticky pellet is achieved, since otherwise the pellet may fall out of the well upon transportation. Otherwise, a sticky sugar such as saccharose or dextrose is to be added to the freezing solution. The plates are packed in sterile manner and with drying agent (Sica) in a light-tight manner. The microtitration plates so prepared could be kept over longer periods of time at room temperature, without this having an influence on the growth capability of the microorganisms.

2. Microbiological Determination

Niacin (nicotinic acid and nicotinic acid amide) was quantitatively determined in foodstuffs. The method is not usable in the case of samples which contain antibiotics or growth hindering substances. Niacytine is not consumed by *Lactobacillus plantarum* (ATCC 8014). The niacin concentration was measured by means of the turbidity caused by bacterial growth in comparison to a standard series.

Material: All glass containers and apparatus for the dilution series was pre-washed by hand with a ca. 1% Tween® 80 solution, then treated with hydrochloric acid (0.1 M) and with NaOH solution (0.1 M), rinsed hot and cold three times with tap water and finally washed with distilled water. The containers and apparatus were dried, provided with suitable closures (metal caps, aluminum foil) and wrapped and treated for more than one hour at least 250° C.

Sample storage: Liquors and other perishable samples were stored cooled up to the time of testing.

Vitamin standard: 10 mg niacin was weighed out with a precision weighing scale into a suitable glass container and, with stirring, dissolved in 100 ml water. The concentration of the thus produced basic solution was 0.1 mg niacin per milliliter (=100000 ng/ml). This solution was then diluted in two steps, first 1:100 and then 1:125, to a final concentration of 40 ng niacin/ml. Further dilution steps were prepared (0.6 ng/150 µl, 1.2 ng/150 µl, 3.6 ng/150 µl, 4.8 ng/150 µl, 6.0 ng/150 µl=standard series).

Sample Preparation. Between 1 and 10 g sample was weighed into a glass container with a stirrer and topped off with water to 100 g. The container was closed and sterilized at 120° C. for 2 minutes. The sample was then so diluted that the niacin concentration to be expected was around 1.2 ng/150 µl. For this purpose the samples were extracted in duplicate with a series of different sample dilutions.

Cultivation: There was added to the wells of a microtitration plate 150 µl standard and sample solution and 150 µl niacin-deficient double concentrated assay medium (niacin medium) and then closed with an air and water non-permeable foil. The cultivation was effected for 48 h at a temperature of 37° C. in an incubator.

The selected temperature was held constant within a range of ±0.5° C. Between the addition of the medium and the beginning of the cultivation there was not more than 30 minutes.

Evaluation: After the end of the cultivation, the turbidity of the standards and the samples on the microtitration plate was measured with an ELISA reader (ELISA photometer) at 630 nm (alternatively 540 nm). From the values of the attempts, a medium value was calculated for the concentration state concerned.

Preparation of the calibration curve: The extinction values of the standard series were plotted on millimeter paper or graphically represented by means of suitable software. The polynomic trend line of the fourth order function associated with the determined data points was calculated. The square of the correlation coefficient of the values must be more than 0.990. The correlation coefficient is thereby calculated as follows:

$$r = \frac{n(\sum xy) - (\sum x)(\sum y)}{\sqrt{[n\sum x^2 - (\sum x)^2][[n\sum y^2 - (\sum y)^2]]}}$$

Calculation: By setting the determined sample extinction values as y in the function equation and by means of the pq-formula, the associated x-value can be calculated. Additionally, the x-value sought can be read of from the graphically produced calibration curve. With sample dilutions having stronger self-turbidity the determined y-values were corrected in comparison to the measured value of a sterile control also carried out. The correction value is yielded by the measurement difference between sterile control and a non-inoculated (turbid) sample after incubation in a water bath.

It is to be recommended in the case of each fifth test to carry out a defined sample as a measure for quality control. The results are to be entered in an average value regulation chart; This chart is to be stored with the current raw data.

Figure 1:
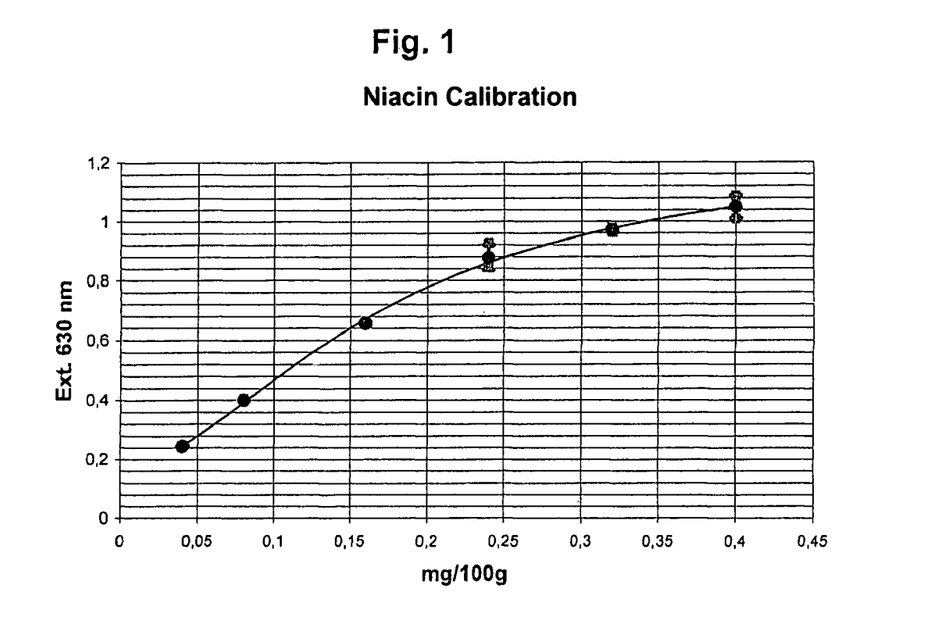
FIGS. 1-7 graphical illustrations of the growth of various microplate dry microorganisms in accordance with the invention in dependence upon the concentration of various vitamins in the test medium concerned in each case.

FIG. 1 shows the determined standard curve after 48 hours incubation of $5 \times 10^4$ dry cells in niacin assay medium. Despite the freeze drying in the microtitration plate and storage for four weeks of the dried microorganism microtitration plate at room temperature, consistent growth curves were obtained with *Lactobacillus plantarum*, which permitted the determination of vitamin $B_3$ in standard and sample.

In a further comparative test, the same number of cells of *Lactobacillus plantarum* was frozen for 72 hours in PBS, 20% glycerine. In the subsequent growth test, although the glycerine stabilized cells were vital, the growth determined correlated in no way with the quantity of niacin in the assay medium. Rather, across all niacin concentrations, there was determined a virtually uniform growth. Here, the growth thus originated in all cases from a few starting cells, that is from a few cells which in the solution had a starting advantage.

This was otherwise in the case of the microorganisms of *Lactobacillus plantarum* dried in accordance with the invention in the presence of a conserving sugar. Here, as the concentration-dependent growth curve shows, all cells contribute to the activity and growth in the added standard and sample solution. The growth curve is then only dependent on the niacin present.

TABLE 1

Determination of the niacin standard curve and 8 samples

| Standard mg/100 g | Measurement at 630 nm | Number | Average value | Standard deviation | Variance (%) |
|---|---|---|---|---|---|
| 0.04 | 0.242 0.247 0.246 | 3 | 0.245 | 0.003 | 1.08 |
| 0.08 | 0.405 0.399 0.398 | 3 | 0.401 | 0.004 | 0.945 |
| 0.16 | 0.653 0.654 0.663 | 3 | 0.657 | 0.006 | 0.839 |
| 0.24 | 0.849 0.926 0.854 | 3 | 0.876 | 0.043 | 4.917 |
| 0.32 | 0.961 0.972 0.979 | 3 | 0.971 | 0.009 | 0.935 |
| 0.4 | 1.055 1.085 1.008 | 3 | 1.049 | 0.039 | 3.699 |

TABLE 1-continued

Determination of the niacin standard curve and 8 samples

| Standard mg/100 g | Measurement at 630 nm | Number | Average value | Standard deviation | Variance (%) |
|---|---|---|---|---|---|
| Sample SPL1 | 0.416 0.413 0.415 | 3 | 0.415 | 0.002 | 0.368 |
| SPL2 | 0.551 0.562 0.556 | 3 | 0.556 | 0.006 | 0.99 |
| SPL3 | 0.898 0.892 0.906 | 3 | 0.899 | 0.007 | 0.782 |
| SPL4 | 1.077 1.102 1.096 | 3 | 1.092 | 0.013 | 1.196 |
| SPL5 | 0.299 0.298 0.295 | 3 | 0.297 | 0.002 | 0.7 |
| SPL6 | 0.394 0.409 0.396 | 3 | 0.4 | 0.008 | 2.038 |
| SPL7 | 0.672 0.674 0.68 | 3 | 0.675 | 0.004 | 0.616 |
| SPL8 | 0.866 0.866 0.866 | 3 | 0.866 | 0 | 0 |

The indications of concentration are in line with the usual indications of content in foodstuffs chemistry. Here, the vitamins of 1 g sample weight were extracted in 100 ml water, 150 µl extract was transferred to a well in the microtitration plate, multiply concentrated test medium added, the quantity of vitamin determined and finally adjusted to a 100 g sample. The standard was correspondingly applied.

Example 2

Folic Acid Determination

The preparation of the microtitration plate and the determination of folic acid (pteroylglutaminic acid and other folic acid conjugates) was effected as in Example 1, except only that *Lactobacillus rhamnosus* ATCC 7469 was employed as test organism. There was employed as assay medium Difco™ folic acid-casein medium, containing activated carbon treated pancreas digested casein 10.0 g/L, dextrose 40.0 g/L, sodium acetate 40.0 g/L, potassium dihydrogen phosphate 1.0 g/L, dipotassium hydrogen phosphate 1.0 g/L, DL-tryptophane 0.2 g/L, L-asparagine 0.6 g/L, L-cystein hydrochloride 0.5 g/L, adenine sulfate 10.0 mg/L, guanine hydrochloride 10.0 mg/L, uracil 10.0 mg/L, xanthin 20.0 mg/L, Polysorbate-80 0.1 g/L, glutathion (reduced) 5.0 mg/L, magnesium sulfate 0.2 g/L, sodium chloride 20.0 mg/L, iron sulfate 20.0 mg/L, manganese sulfate 15.0 mg/L, riboflavin 1.0 mg/L, p-aminobenzoic acid 2.0 mg/L, pyridoxine hydrochloride 4.0 mg/L, thiamine hydrochloride 400.0 µg/L, calcium pantothenate 800.0 µg/L, nicotinic acid 800.0 µg/L, biotin 20.0 µg/L, 0.05% ascorbic acid. The storage medium contained 200 mM trehalose. The folic acid standard was dissolved in 100 mMol potassium phosphate buffer, pH 6.1, 0.1% ascorbic acid.

TABLE 2

Folic acid standard curve

| Standard pg/ 150 µl | Standard µg/ 100 g | Measurement at 630 nm | Number | Average value | Standard deviation | Variance (%) |
|---|---|---|---|---|---|---|
| 3.75 | 0.25 | 0.261 0.261 0.269 | 3 | 0.264 | 0.005 | 1.752 |
| 7.5 | 0.5 | 0.556 0.536 0.544 | 3 | 0.545 | 0.01 | 1.846 |
| 15 | 1 | 0.784 0.788 0.807 | 3 | 0.793 | 0.012 | 1.55 |
| 22.5 | 1.5 | 0.986 1.002 1.01 | 3 | 0.999 | 0.012 | 1.223 |
| 30 | 2 | 1.121 1.074 1.087 | 3 | 1.094 | 0.024 | 2.218 |

Figure 2:
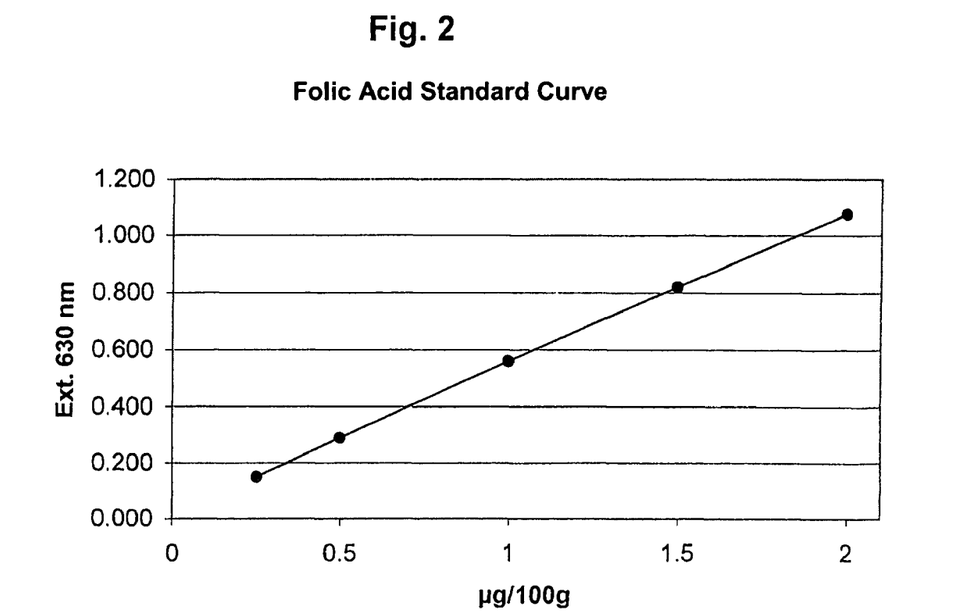

The determined standard curve is graphically illustrated in FIG. 2.

Example 3

Vitamin $B_{12}$ Determination

The preparation of the microtitration plate and the determination of vitamin $B_{12}$ (cyanocobalamine, hydroxycobalamine) was effected as in Example 1, except only that *Lactobacillus delbrueckii* subsp. *Lactis* (*L. leichmanii*) ATCC 7830 was employed as test organism. As assay medium there served Difco™ $B_{12}$ assay medium, containing casamino acids 15.0 g/L, dextrose 40.0 g/L, asparagine 0.2 g/L, sodium acetate 20.0 g/L, Ascorbic acid 4.0 g/L, L-cystein 4.0 g/L, DL-tryptophane 0.4 g/L, adenine sulfate 20.0 mg/L, guanine hydrochloride 20.0 mg/L, uracil 20.0 mg/L, xanthin 20.0 mg/L, polysorbate-80 2.0 g/L, magnesium sulfate (waterfree) 0.4 mg/L, sodium chloride 20.0 mg/L, iron sulfate 20.0 mg/L, manganese sulfate 20.0 mg/L, riboflavin 1.0 mg/L, p-aminobenzoic acid 2.0 mg/L, pyridoxine hydrochloride 4.0 mg/L, thiamine hydrochloride 1.0 mg/L, calcium pantothenate 1.0 mg/L, niacin 2.0 mg/L, biotin 10.0 ug/L, pyridoxine hydrochloride 4.0 mg/L, pyridoxal hydrochloride 4.0 mg/L, pyridoxamine hydrochloride 800.0 ug/L, folic acid 200.0 pg/L, potassium dihydrogen phosphate 1.0 g/L, dipotassium hydrogen phosphate 1.0 g/L. The storage medium further contained 200 mM trehalose.

TABLE 3

Vitamin $B_{12}$ standard curve

| Standard µg/100 g | Measurement at 630 nm | Number | Average value | Standard deviation | Variance (%) |
|---|---|---|---|---|---|
| 0.1 | 0.264 0.271 0.269 | 3 | 0.268 | 0.004 | 1.345 |
| 0.2 | 0.531 0.51 0.503 | 3 | 0.515 | 0.015 | 2.831 |
| 0.3 | 0.727 0.721 0.736 | 3 | 0.728 | 0.008 | 1.037 |
| 0.4 | 0.88 0.863 0.865 | 3 | 0.869 | 0.009 | 1.069 |
| 0.8 | 1.086 1.073 1.048 | 3 | 1.069 | 0.019 | 1.807 |

Figure 3:
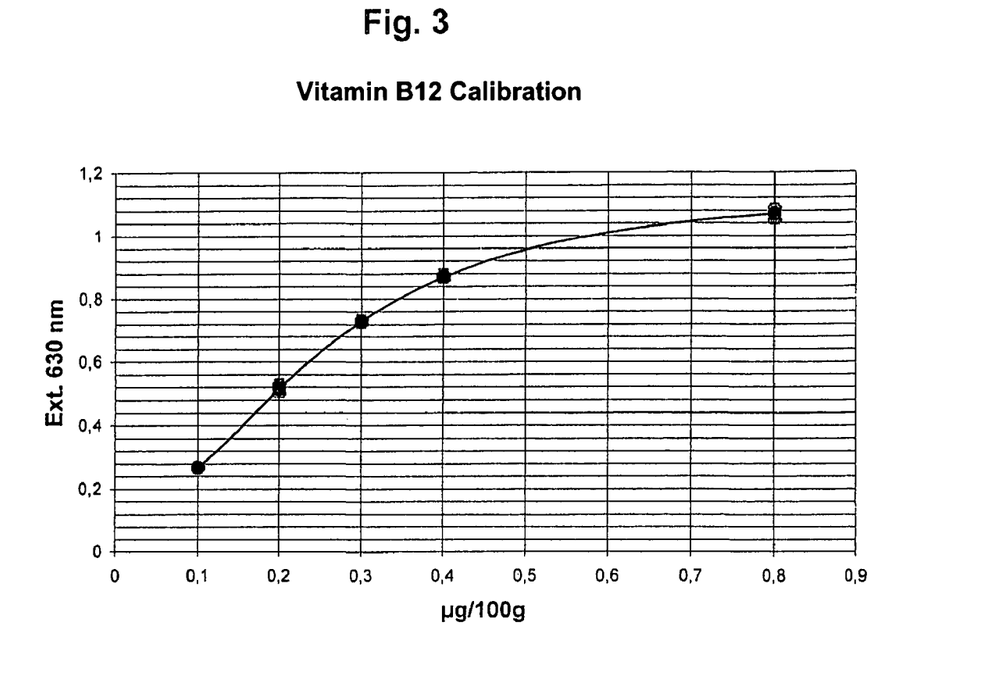

The determined vitamin $B_{12}$ standard curve is graphically illustrated in FIG. 3.

Example 4

Biotin Determination

The preparation of the microtitration plate and determination of biotin was effected as in Example 1 with *Lactobacillus plantarum* ATCC 8014. There served as assay medium Difco™ biotin assay medium, containing casamino acids 12.0 g/L, dextrose 40.0 g/L, sodium acetate 20.0 g/L, L-cystein 0.2 g/L, DL-tryptophane 0.2 g/L, adenine sulfate 20.0 mg/L, guanine hydrochloride 20.0 mg/L, uracil 20.0 mg/L, thiamine hydrochloride 2.0 mg/L, riboflavin 2.0 mg/L, niacin 2.0 mg/L, calcium pantothenate 2.0 mg/L, pyridoxine hydrochloride 4.0 mg/L, p-aminobenzoic acid 0.2 mg/L, magnesium sulfate (water-free) 0.4 mg/L, sodium chloride 20.0 mg/L, iron sulfate 20.0 mg/L, manganese sulfate 20.0 mg/L, potassium dihydrogen phosphate 1.0 g/L, dipotassium hydrogen phosphate 1.0 g/L. The storage medium further contain 200 mM trehalose. The determined standard curve is show in FIG. 4.

TABLE 4

Biotin standard curve

| Standard µg/100 g | Measurement at 630 nm | Number | Average value | Standard deviation | Variance (%) |
|---|---|---|---|---|---|
| 0.003 | 0.205 0.204 0.203 | 3 | 0.204 | 0.001 | 0.49 |
| 0.009 | 0.491 0.506 0.5 | 3 | 0.499 | 0.008 | 1.513 |
| 0.015 | 0.676 0.693 0.686 | 3 | 0.685 | 0.009 | 1.247 |
| 0.021 | 0.826 0.822 0.82 | 3 | 0.823 | 0.003 | 0.371 |
| 0.027 | 0.986 0.988 0.982 | 3 | 0.985 | 0.003 | 0.31 |

Figure 4:
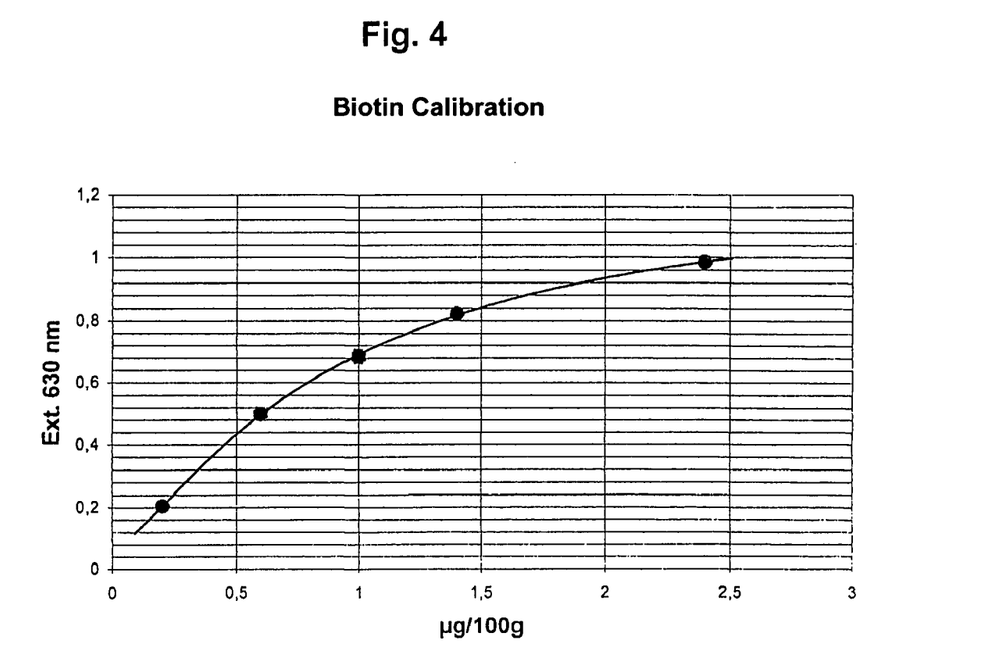

The associated standard curve is shown in FIG. 4.

Example 5

$B_6$ Pyridoxine Determination

Figure 5:
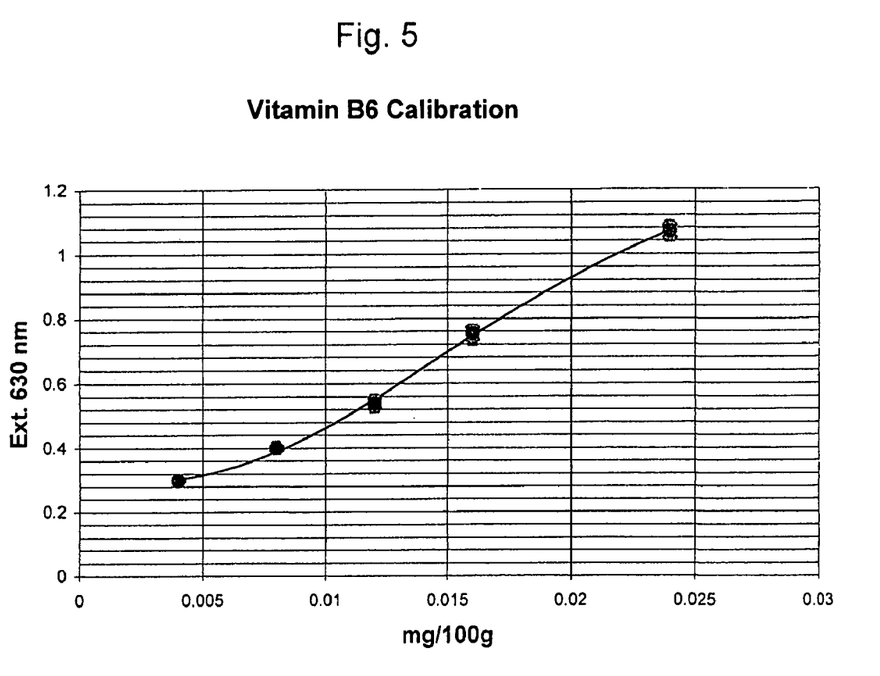

The preparation of the microtitration plate and the determination of B6-pyridoxine was effected as in Example 1, except only that as test organism *Saccharomyces cerevisae* ATCC 9080 was employed. As assay medium there was employed Difco™ pyridoxine-Y-medium, containing dextrose 40.0 g/L, L-asparagine 4.0 g/L, ammonium sulfate 4.0 g/L potassium dihydrogen phosphate 3.0 g/L, magnesium sulfate 1.0 g/L, calcium chloride 0.49 g/L, DL-methionine 40.0 mg/L, DL-tryptophane 40.0 mg/L, DL-isoleucin 40.0 mg/L, DL-valin 40.0 mg/L, L-histidine hydrochloride 20.0 mg/L, riboflavin 20.0 mg/L, biotin 8.0 mg/L, inositol 5.0 mg/L, iron sulfate 500 µg/L, thiamine hydrochloride 400.0 µg/L, calcium pantothenate 400.0 µg/L, nicotinic acid 400.0 µg/L, boric acid 200.0 µg/L, potassium iodide 200.0 µg/L, ammonium molybdate 40.0 µg/L, manganese sulfate 80.0 µg/L, copper sulfate 90.0 µg/L, zinc sulfate 80.0 µg/L. The storage medium further contained 200 mM trehalose. The determined standard curve is shown in FIG. 5.

TABLE 5

$B_6$-pyridoxine standard curve

| Standard mg/100 g | Measurement at 630 nm | Number | Average value | Standard deviation | Variance (%) |
|---|---|---|---|---|---|
| 0.004 | 0.298 0.297 0.301 | 3 | 0.299 | 0.002 | 0.697 |
| 0.008 | 0.394 0.407 0.398 | 3 | 0.4 | 0.007 | 1.666 |
| 0.012 | 0.522 0.541 0.552 | 3 | 0.538 | 0.015 | 2.819 |
| 0.016 | 0.73 0.766 0.762 | 3 | 0.753 | 0.02 | 2.622 |
| 0.024 | 1.049 1.088 1.07 | 3 | 1.069 | 0.02 | 1.826 |

Example 6

Calcium Panthothenate Determination

Figure 6:
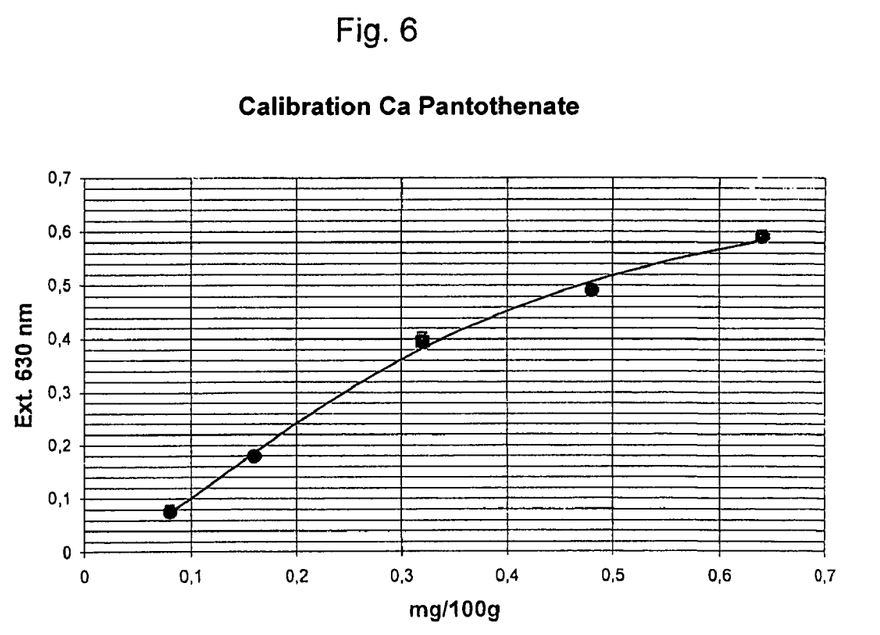

The preparation of the microtitration plate and the determination of calcium pyridoxine 800 µg/L, p-aminobenzoic acid 200.0 µg/L, biotin 1.0 µg/L, potassium dihydrogen phosphate 1.0 g/L, dipotassium hydrogen phosphate 1.0 g/L, magnesium sulfate 0.4 g/L, sodium chloride 20.0 mg/L, iron sulfate 20.0 mg/L, manganese sulfate 20.0 mg/L. The storage medium further contained 200 mM trehalose. The determined standard curve is shown in FIG. 6.

TABLE 6

Ca pantothenate standard curve

| Standard mg/100 g | Measurement at 630 nm | Number | Average value | Standard deviation | Variance (%) |
|---|---|---|---|---|---|
| 0.08 | 0.075 0.08 0.073 | 3 | 0.076 | 0.004 | 4.744 |
| 0.16 | 0.181 0.179 0.178 | 3 | 0.179 | 0.002 | 0.852 |
| 0.32 | 0.389 0.404 0.392 | 3 | 0.395 | 0.008 | 2.009 |
| 0.48 | 0.49 0.493 0.491 | 3 | 0.491 | 0.002 | 0.311 |
| 0.64 | 0.589 0.594 0.588 | 3 | 0.59 | 0.003 | 0.545 |

Example 7

Riboflavin Determination

The preparation of the microtitration plate and the determination of riboflavin was effected as in Example 1, except only that *Lactobacillus rhamnosus* ATCC 7469 was employed as test organism. As assay medium there was employed Difco™ riboflavin assay medium, containing cas amino acids 10.0 g/L, dextrose 20.0 g/L, sodium acetate 15.0 g/L, dipotassium hydrogen phosphate 1.0 g/L, potassium dihydrogen phosphate 1.0 g/L, L-asparagine 0.6 g/L, L-cystine 0.2 g/L, DL-tryptophane 0.2 g/L, magnesium sulfate 0.4 g/L, adenine sulfate 20.0 mg/L, guanine hydrochloride 20.0 mg/L, uracil 20.0 mg/L, xanthin 20 mg/L, iron sulfate 20.0 mg/L, manganese sulfate 20.0 mg/L, sodium chloride 20.0 mg/L, pyridoxine hydrochloride 4.0 mg/L, pyridoxal hydrochloride 4.0 mg/L, p-aminobenzoic acid 2.0 mg/L, calcium pantothenate 800 µg/L, folic acid 800 µg/L, nicotinic acid 800 µg/L, thiamine hydrochloride 400 µg/L, biotin 1.0 µg/L. The storage medium additionally contained 200 mM trehalose.

TABLE 7

$B_2$ Riboflavin-standard curve

| Standard mg/100 g | Measurement at 630 nm | Number | Average value | Standard deviation | Variance (%) |
|---|---|---|---|---|---|
| 0.1 | 0.196 | 3 | 0.204 | 0.007 | 3.342 |
|  | 0.209 |  |  |  |  |
|  | 0.206 |  |  |  |  |
| 0.2 | 0.383 | 3 | 0.398 | 0.013 | 3.371 |
|  | 0.404 |  |  |  |  |
|  | 0.408 |  |  |  |  |
| 0.3 | 0.624 | 3 | 0.623 | 0.006 | 0.981 |
|  | 0.616 |  |  |  |  |
|  | 0.628 |  |  |  |  |
| 0.4 | 0.752 | 3 | 0.759 | 0.01 | 1.345 |
|  | 0.755 |  |  |  |  |
|  | 0.771 |  |  |  |  |
| 0.5 | 0.855 | 3 | 0.88 | 0.023 | 2.616 |
|  | 0.886 |  |  |  |  |
|  | 0.9 |  |  |  |  |

Figure 7:
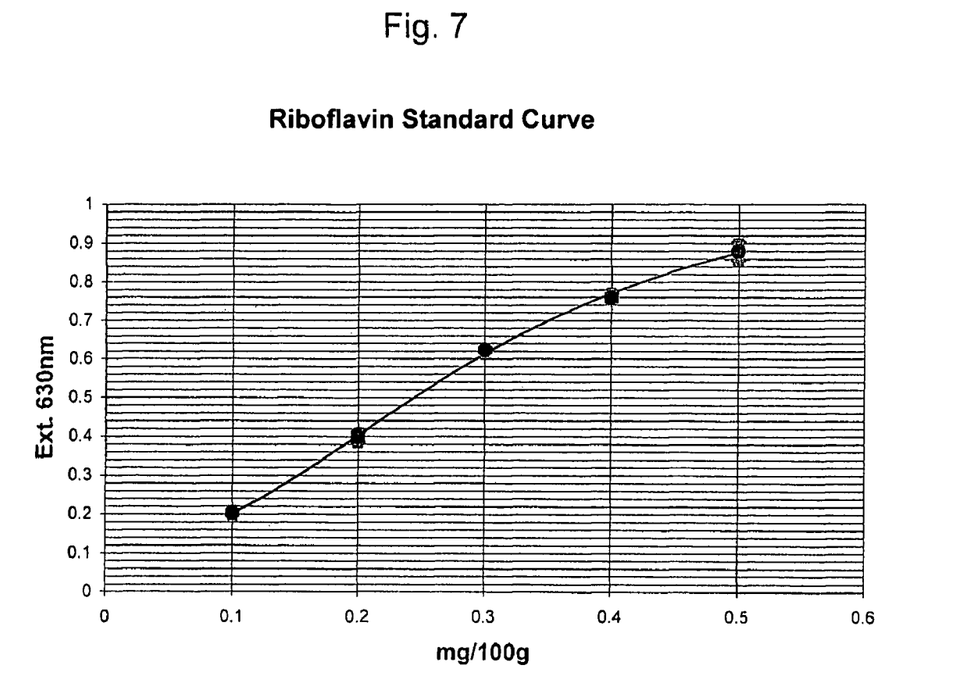

The determined standard curve is shown in FIG. 7.

Example 7

Thiamine (Vitamin B1)
Determination—Hypothetical

The preparation of the microtitration plate and the determination of riboflavin was effected as in Example 1, except only that *Weissella virdescens* ATCC 12706 was employed as test organism. As assay medium there was employed Difco™ thiamine assay medium LV, containing thiamine-free yeast extract 10.0 g/L, thiamine-free trypton 20 g/L, dextrose 20.0 g/L, sodium citrate 10.0 g/L, dipotassium hydrogen phosphate 10.0 g/L, sodium chloride 10.0 g/L, magnesium sulfate 1.6 g/L, iron sulfate 0.08 g/L, manganese sulfate 0.28 g/L, polysorbate-80 2.0 g/L. The freezing medium additionally contained 200 mM trehalose.
The scope of protection of the invention is provided by the following claims, which likewise belong to the disclosure.

The invention claimed is:
1. Method for quantitative microbiological determination of individual vitamins, amino acids, or other substances to be tested that are necessary for life in a substance mixture comprising:
providing a microtitration plate for microbiological growth and metabolism determination having wells, wherein the respective wells are provided with a predetermined number of viable cells of a suitable microorganism which provide a reproducible growth curve, and wherein the microorganism is in a freeze dried condition in a freezing and storage medium comprising trehalose, sucrose or a mixture of trehalose and sucrose, and which medium is deficient in the substance to be tested,
adding water and a substance to be tested comprising an individual vitamin, amino acid, or other substance to be tested that is necessary for life, and
determining quantitatively the levels of vitamin, amino acid, or other substance to be tested that is necessary for life in the test substance by measuring microorganism growth against at least one standard solution of the vitamin, amino acid, or other substance to be tested.
2. The method according to claim 1, wherein the freezing and storage medium comprises an amount of the test medium for the microbiological determination.
3. The method according to claim 1, wherein the substance to be determined is selected from the group consisting of vitamin $B_3$ (niacin, nicotinic acid, nicotinic acid amide), vitamin $B_{12}$ (cyanocobalamin, hydroxycobalamin), folic acid (folic acid, pteroylglutaminic acid, folic acid conjugate), biotin, pantothenic acid (pantothenic acid, panthenol), vitamin $B_1$ (thiamine, thiamine pyrophosphate), vitamin $B_2$ (riboflavin, riboflavin phosphate), vitamin $B_6$ (pyridoxine, pyridoxal, pyridoxamine, pyridoxal-5'-phosphate), lysine, methionine, cysteine, choline and inositol.
4. The method according to claim 1, wherein the microorganism is selected from the group consisting of *Lactobacillus delbrueckii* subsp. *lactis, Enterococcus hirae, Lactobacillus plantarum, Lactobacillus fermenti, Lactobacillus helveticus* and *L. veridesceno Streptococcus faecalis*.
5. The method according to claim 1, wherein the quantitative determination of the levels of vitamin, amino acid, or other substance necessary for life in the test substance is carried out using a run-off method.
6. The method according to claim 1, wherein the substance to be determined is selected from the group consisting of vitamin $B_3$ (niacin, nicotinic acid, nicotinic acid amide) and the microorganism is *Lactobacillus plantarum*.
7. The method according to claim 5, wherein the substance to be determined is selected from the group consisting of vitamin $B_3$ (niacin, nicotinic acid, nicotinic acid amide) and the microorganism is *Lactobacillus plantarum*.
8. The method according to claim 1, wherein said microtitration plate is stored dry at room temperature prior to the step of adding water and the substance to be tested.
9. The method according to claim 1, wherein said microtitration plate is stored dry for at least 12 months prior to the step of adding water and the substance to be tested.

* * * * *